US00PP20772P3

(12) United States Plant Patent
Hall et al.

(10) Patent No.: US PP20,772 P3
(45) Date of Patent: Feb. 23, 2010

(54) RASPBERRY PLANT NAMED 'KORERE'

(50) Latin Name: ***Rubus idaeus* L.**
Varietal Denomination: Korere

(75) Inventors: Harvey K. Hall, Motueka (NZ); Joseph Stephens, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/214,361

(22) Filed: Jun. 18, 2008

(65) Prior Publication Data

US 2008/0320623 P1 Dec. 25, 2008

Related U.S. Application Data

(60) Provisional application No. 60/936,233, filed on Jun. 19, 2007.

(51) Int. Cl.
*A01H 5/00* (2006.01)

(52) U.S. Cl. ..... Plt./204

(58) Field of Classification Search ..... Plt./204
See application file for complete search history.

*Primary Examiner*—Susan B McCormick Ewoldt
(74) *Attorney, Agent, or Firm*—Greenlee Winner and Sullivan PC

(57) ABSTRACT

A new and distinct floricane fruiting red raspberry, *Rubus idaeus* L., variety is described. The variety results from selection among a population of seedlings derived from controlled pollination crossing of the raspberry variety known as 'Moutere' (U.S. Plant Pat. No. 17,744) and the unreleased raspberry selection with the breeder code D188 (not patented). This new variety is characterized by excellent fruit quality, very good shelf life, and an early harvest season, and is suitable for both machine and hand harvest. The new variety appears suitable for the fresh fruit market and has been named 'Korere'.

7 Drawing Sheets

Genus and species of plant claimed: *Rubus idaeus* L.
Variety denomination: Korere.

BACKGROUND TO THE INVENTION

The new variety of red raspberry, *Rubus idaeus* L., was created in the course of a planned breeding program carried out at Nelson, Motueka, New Zealand. The parents used to make the cross in 1991, were the variety 'Moutere' (seed parent) (U.S. Plant Pat. No. 17,744) and the unreleased selection 'D188' (pollen parent) (unpatented).

Seed from this cross was grown and the original plant of the new variety was selected during the 1994–95 summer (Southern Hemisphere) and was found to exhibit:

(a) a spine-free upright growth habit of strong vigor,
(b) the ability to form attractive red fruit of good flavor in high yields on medium length fruiting laterals that ripen very early season, and
(c) resistance to Raspberry Bushy Dwarf Virus (RBDV).

The new variety was first asexually propagated in 1999, at Motueka, Nelson, New Zealand, being reproduced by vegetative cuttings arising from root cuttings. Cuttings developed this way in spring, root within a 3–4 week propagation period, and thus plants suitable for field planting are then ready in autumn of the same year. The resulting plants propagated true to type, demonstrating that the characteristics of the new cultivar are stable and are transmitted without change through succeeding generations. Since 2000, 'Korere' has been asexually propagated in vitro via tissue culture methods. The cultivar has propagated true to type via these means.

SUMMARY OF THE INVENTION

The new variety was selected from a population of seedlings derived from crossing the raspberry variety known as 'Moutere' (U.S. Plant Pat. No. 17,744) and the unreleased raspberry selection with the breeder code D188 (not patented). The new variety was assigned the breeder code, 91318RKB-2 (subsequently coded HR121 at the advanced selection stage). The new variety has since been named 'Korere'.

The new variety was tested and evaluated during the years 1996 to 2005 in the Nelson Region, New Zealand (41.10° S., 172.97° E.). The new variety has also been observed in test plots in Washington State, United States of America (USA).

When compared to the parent 'Moutere', fruit of the new variety was found to ripen significantly earlier in the season, removed from the receptacle easier, and was smaller in size. 'Korere' is further distinguished from 'Moutere' by having canes that have no spines.

When compared to the parent 'D188', the new variety exhibited fruit that are larger and more conical in shape. 'Korere' also has no spines on canes compared to 'D188' that has spines present.

Data collected during the evaluation period comparing fruiting performance of the new variety with standard New Zealand cultivars is presented in Table 1.

TABLE 1

Comparison of fruiting and shelf life performance.

| | 2003/04 season | | | 2005/06 season | | |
|---|---|---|---|---|---|---|
| Variety | Yield[1] (T/ha) | Berry weight (g) | Shelf life[2] | Yield[1] (T/ha) | Berry weight (g) | Shelf life[2] |
| 'Tadmor' | 25.9 | 4.5 | 36 | 13.7 | 4.7 | 50 |
| 'Korpiko' | 14.8 | 4 | 45 | 17.2 | 5.3 | 27 |

TABLE 1-continued

Comparison of fruiting and shelf life performance.

| | 2003/04 season | | | 2005/06 season | | |
|---|---|---|---|---|---|---|
| Variety | Yield[1] (T/ha) | Berry weight (g) | Shelf life[2] | Yield[1] (T/ha) | Berry weight (g) | Shelf life[2] |
| 'Tulameen' | 17.1 | 4.1 | 63 | 12.9 | 4.2 | 76 |
| 'Motueka' | 21.3 | 2.7 | | 15.3 | 3.8 | |
| 'Moutere' | 17.4 | 3 | 63 | 14.2 | 4.5 | 48 |
| 'Korere' | 19.5 | 2.8 | 30 | 13.20 | 3.80 | 48 |
| 'Awaroa'[3] | 15.6 | 3.1 | | 14.4 | 4.1 | 62 |

[1]Hand-picked
[2]Mean (10 berries × 3 reps × 3 harvests) cumulative percentage of berries with rot caused by *Botrytis* after 72 hours on the shelf at ambient temperatures (15-20° C.).
[3]'Awaroa' is a dual cropper i.e. the fruit is borne on both the current and previous year's growth; the data shown in Table 1 indicates the floricane fruit yield only.

Berries of the new variety are suitable for hand picking and consumption as early season fresh fruit. As well as this 'Korere' will machine harvest, however, fruit color may be considered a little light for some processing products in some markets.

BRIEF DESCRIPTION OF THE DRAWINGS

The accompanying photographs show typical specimens of the plant, foliage and fruit of the new variety as depicted in colors as nearly true as is reasonably possible to make the same in a color illustration of this character. The photographs were taken on mature plants in Nelson Region in New Zealand and Washington State, USA.

DETAILED DESCRIPTION

Figure 1:
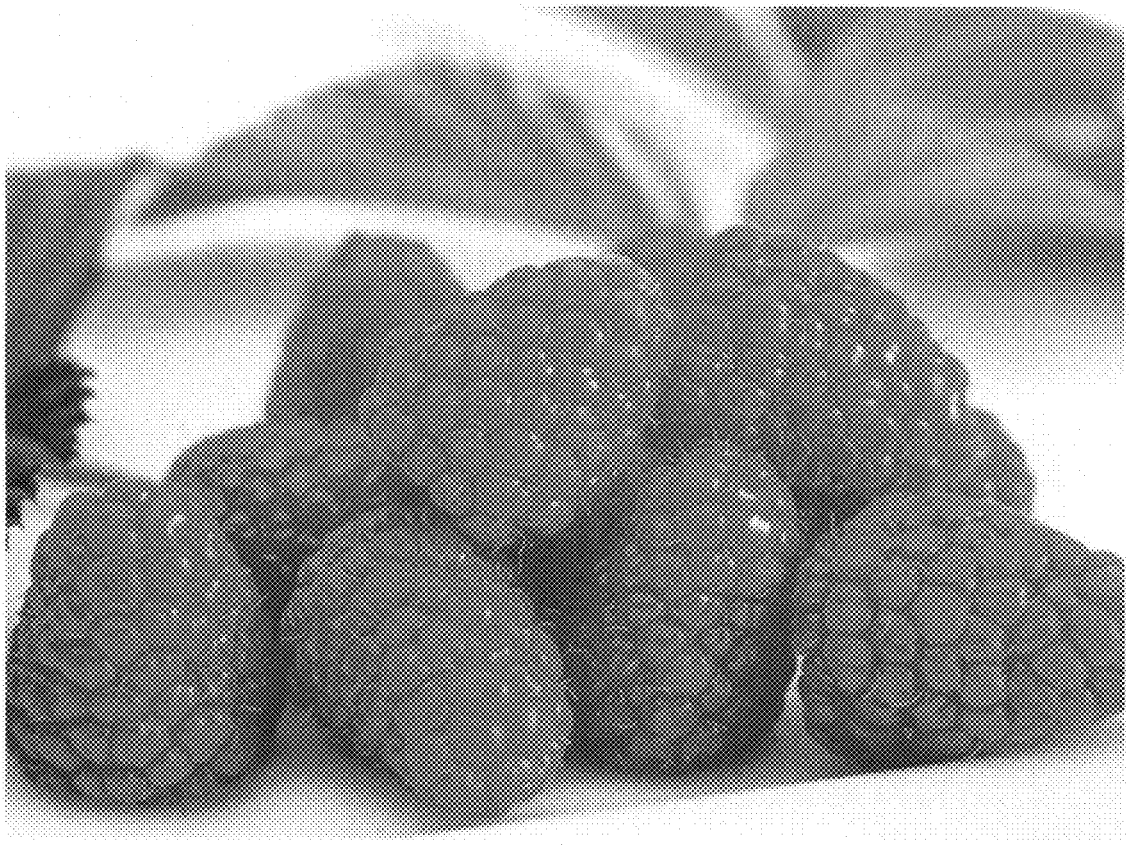
FIG. 1 shows fruit of the variety 'Korere'.
Figure 2:
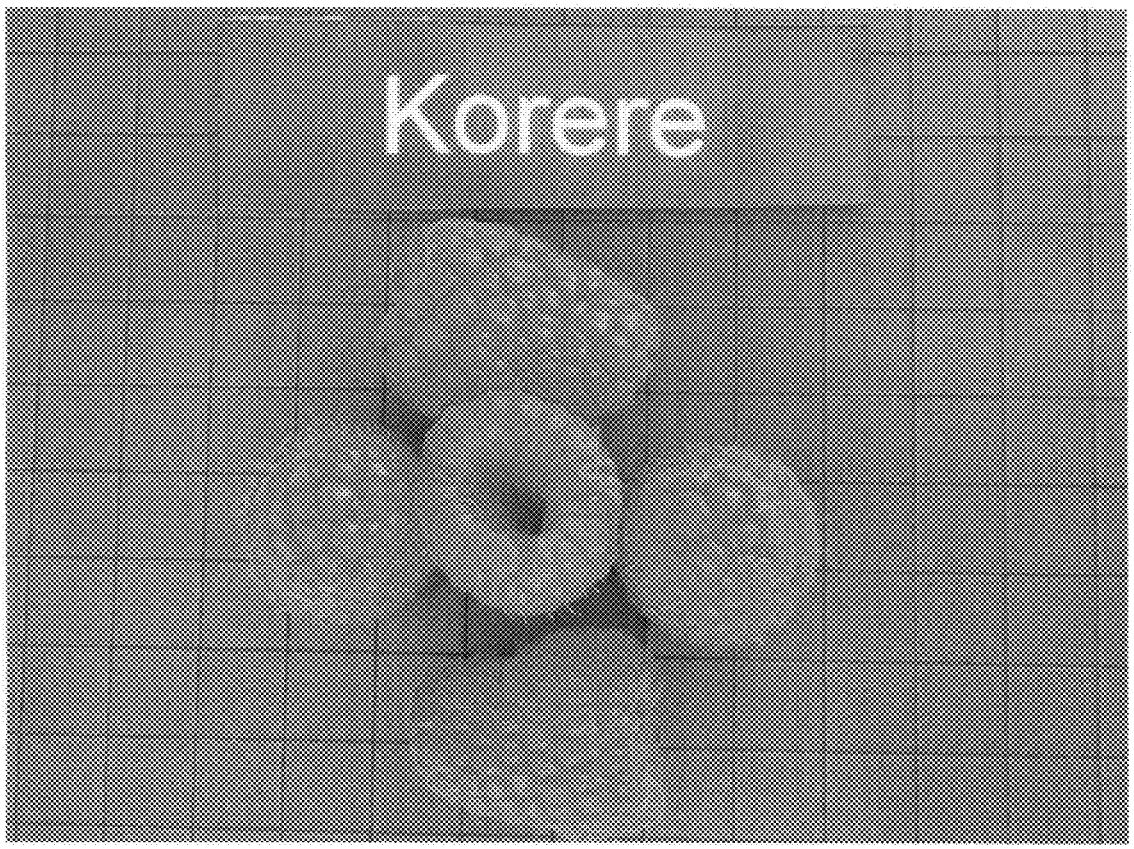
FIG. 2 shows enlarged, close-up, side, and end views of typical samples of individual fruit of the variety 'Korere'.

Horticultural terminology is used in accordance with UPOV guidelines for raspberry. All dimensions in millimeters, weights in grams (unless otherwise stated). Where a colour reference is given these refer to The R.H.S. Colour Chart, The Royal Horticultural Society, London. 4th Edition, 2001. The specimens described were grown at Nelson, New Zealand, and in Washington State, USA.

Environmental data for the New Zealand growing area demonstrates conditions in spring and early summer (equating to the harvest period for the variety) as follows:

Spring (September/October); mean daily temperature in the range 10–12° C. (mean daily minimum 5.8° C., mean daily maximum 16.5° C.).

Early summer (December/January); mean daily temperature 16.8° C. (mean daily minimum 11.1° C., mean daily maximum 22.4° C.).

A cool temperate area, frost conditions are typically experienced in winter, with the lowest winter air temperature unlikely to be colder than −6° C. Average annual rainfall is approximately 1125 mm.

Figure 4:
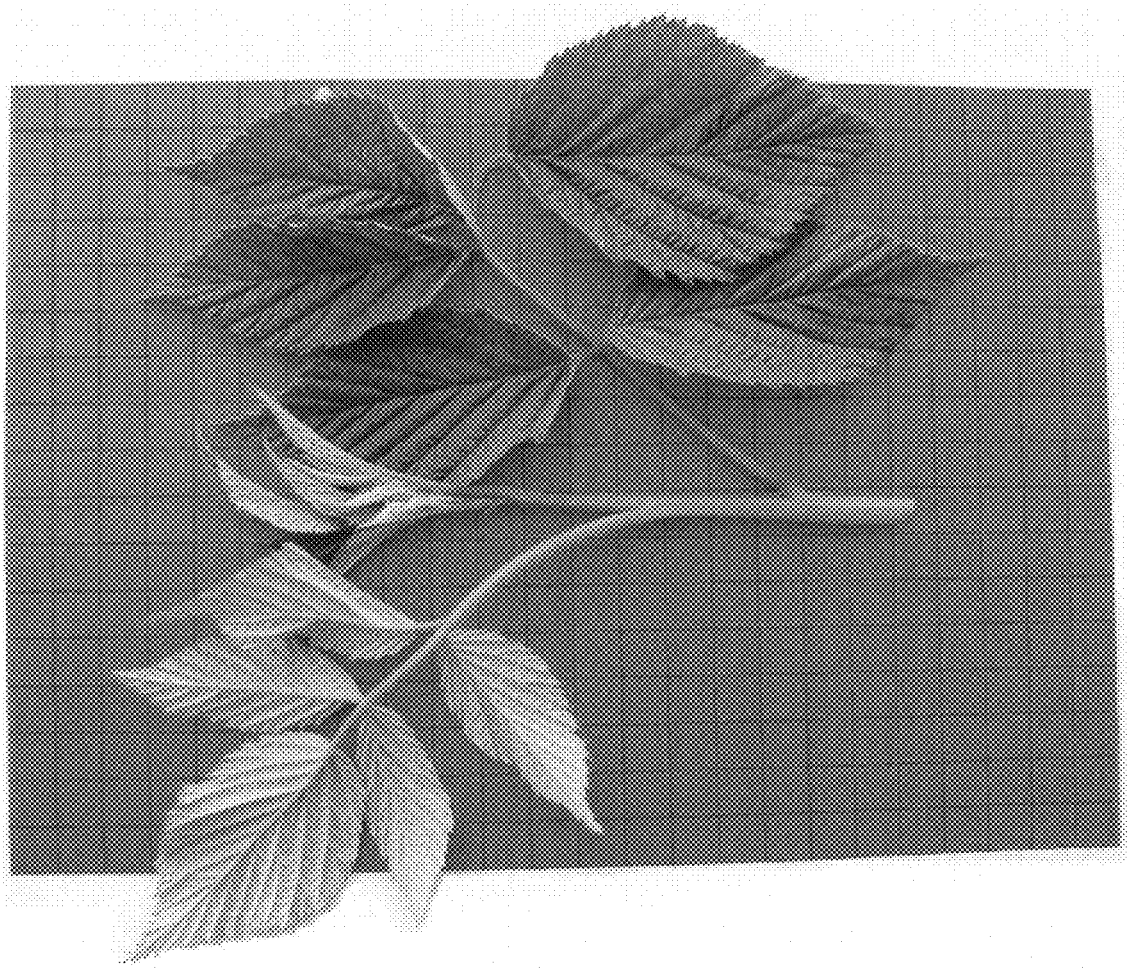
FIG. 4 shows the leaf and shoot tip of a fruiting lateral of the variety 'Korere'; view is of the upper and lower surfaces.
Figure 5:
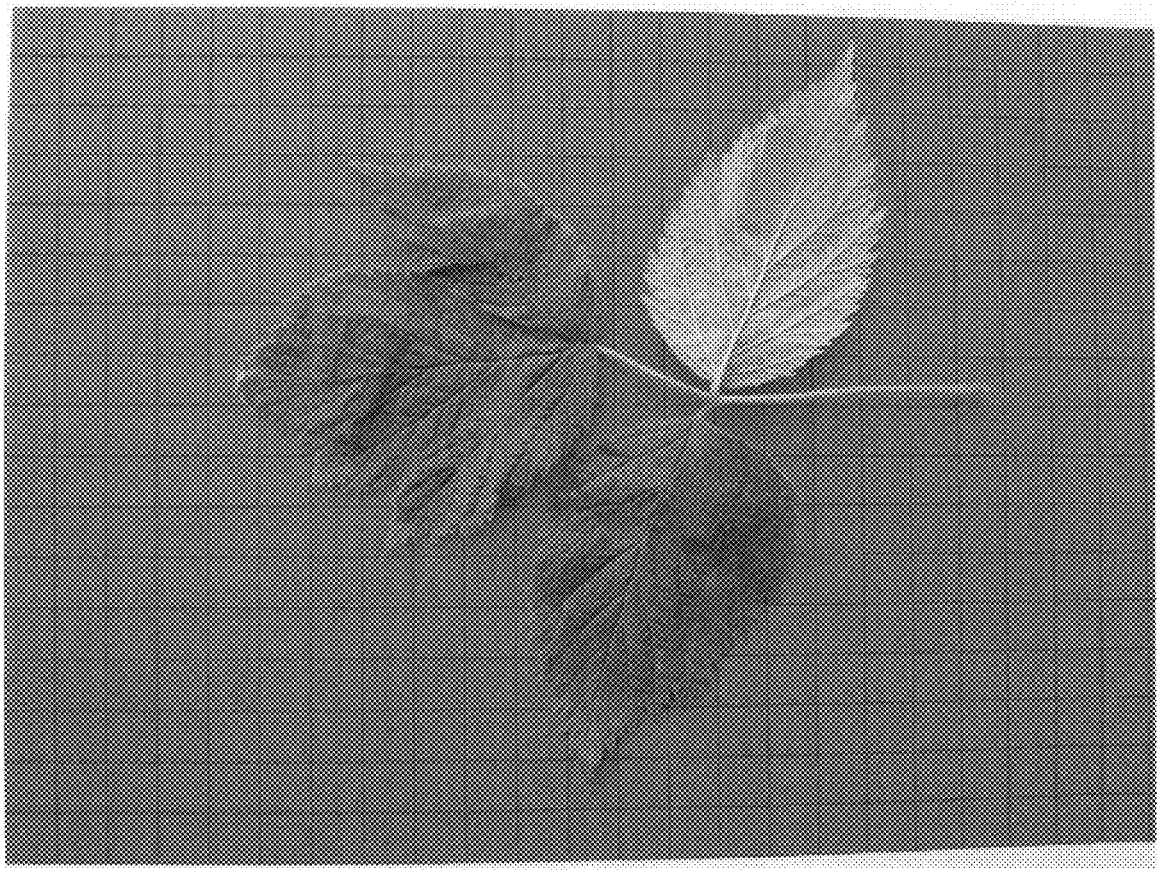
FIG. 5 shows a floricane leaf of the variety 'Korere'; view is of the upper and lower leaf surfaces.
Figure 6:
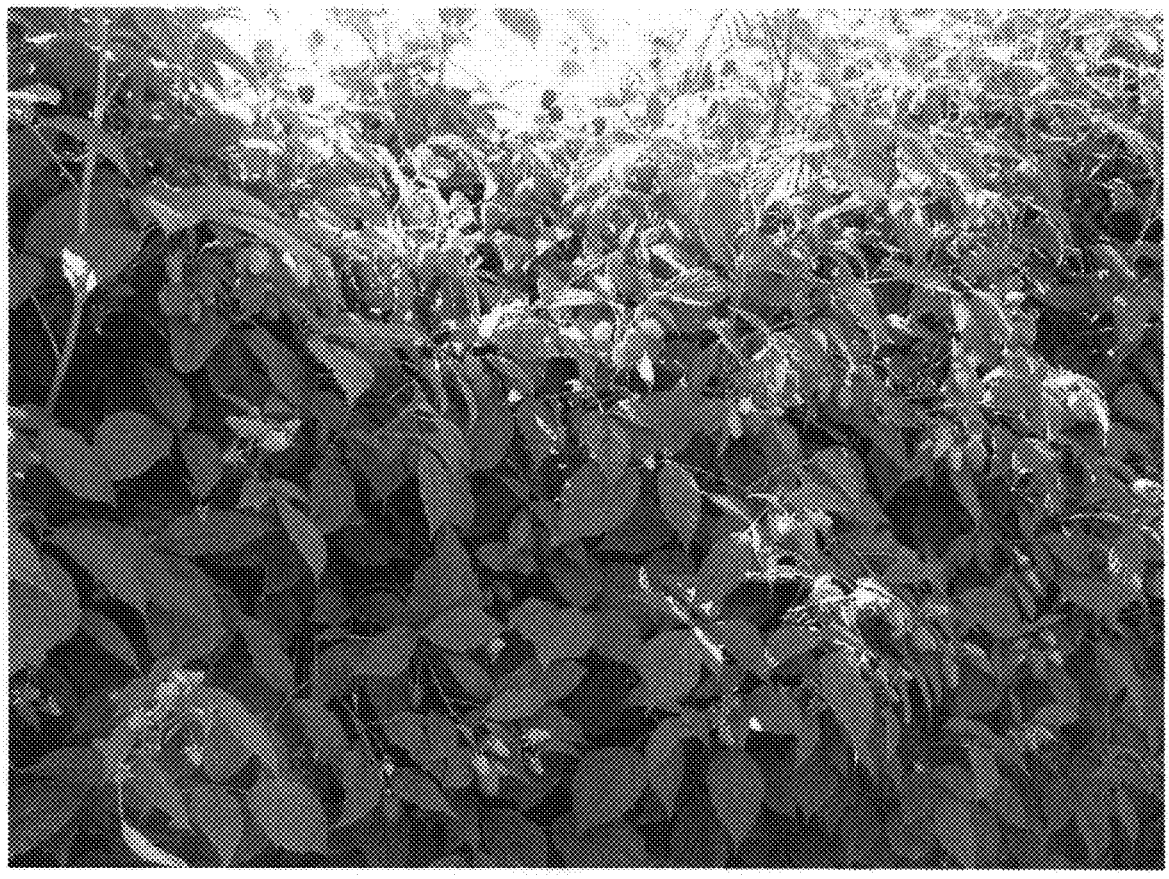
FIG. 6 shows a fruiting plant of the variety 'Korere'; the view displays the fruit, high productivity, and the productive, medium length fruiting laterals.
Figure 7:
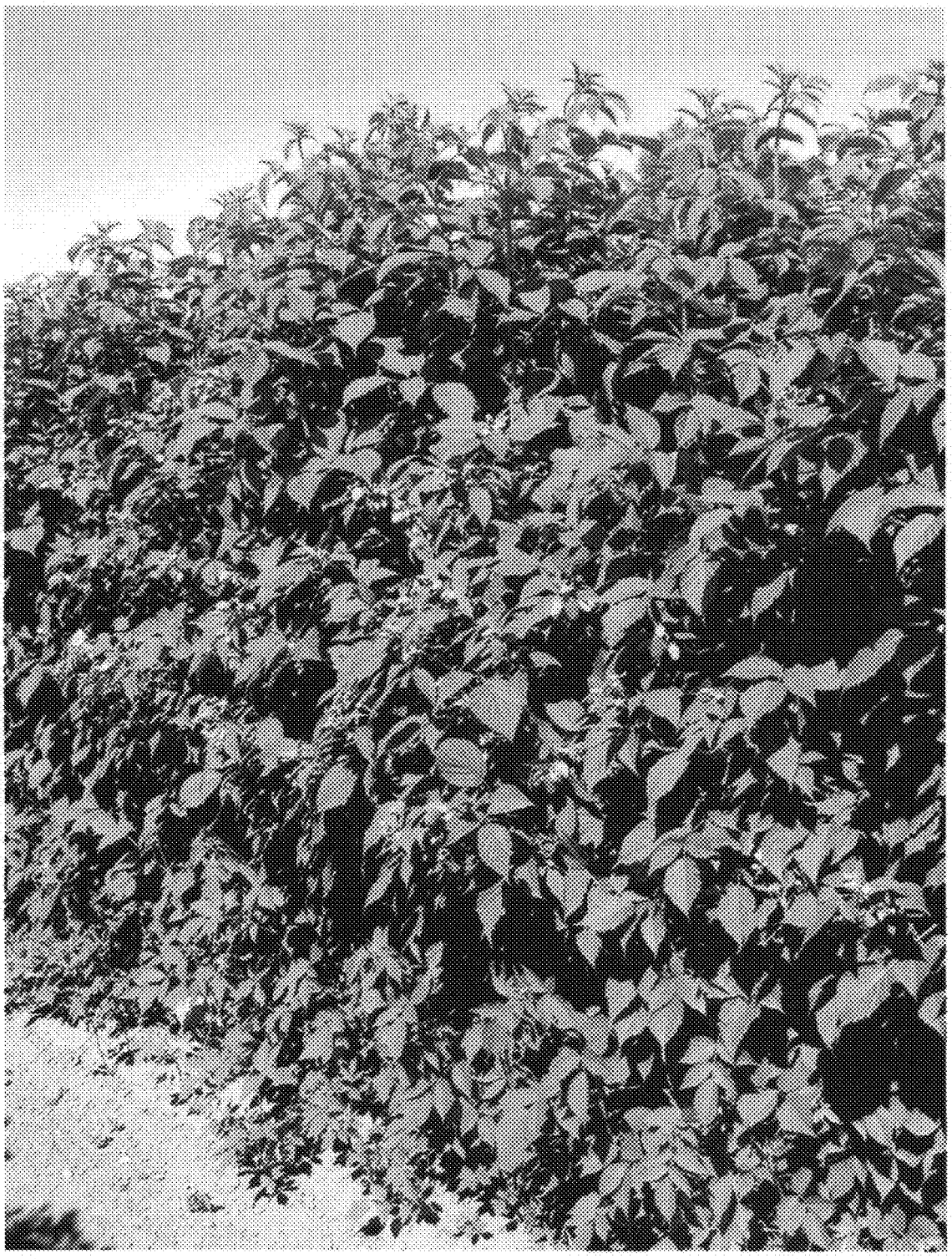
FIG. 7 shows fruit of the variety 'Korere' on the plant in the field; the view displays the upright nature of the canes at full canopy development.

Plant and foliage: plants exhibit an upright growth habit (FIG. 7). Mature plant height is commonly in the range 1800 mm to 2200 mm, although this may vary with the growing conditions. Good vigor is exhibited and internode length is quite short typically in the range 50–60 mm. Plants have many young shoots and canes have no spines (prickles/thorns). Canes are not pubescent indicating the absence of gene H. Canes typically show light brown-tan coloration (near Greyed-orange 175A and 175C) in winter. During the growing season some purple coloration (near Red-purple 59A) is evident on the sun-exposed side of the cane. Plants of 'Korere' have been observed to be less spiny compared with some other commercial varieties, for instance, 'Fairview' (not patented) which has spines. Young shoots are erect, are numerous in number and are near Yellow-green 144A in color. Fruiting laterals are medium in length, typically 300–400 mm long. 'Korere' has distinctive anthocyanin coloration on exposed sides of primocanes, fruiting laterals and pedicels. The anthocyanin coloration can be typically described as shades of Red-purple 59A. The leaves are compound, moderately crinkled, flat and glossy, with strong silver coloration on the leaf underside. (FIGS. 4 and 5). The coloration of the upper surface of the leaf is green (near Green 137A), the under side being markedly lighter in coloration (near Greyed-green 194A). The number of primocane leaflets per internode is predominantly five. The base of the terminal leaflet is ovate in shape and typically averages 60 mm in diameter and 90 mm in length. While the leaves do not have distinguished marginal or vein coloration, the venation has noticeable rises and falls, and the leaf margin is typically serrate. The leaf petiole typically averages approximately 40–50 mm in length and 2.3 mm in diameter. It is near Yellow-green 145B in color. The fruit is borne on the previous year's growth. The fruiting laterals are medium short in length, commonly measuring 300–400 mm, and are weakly ascending and horizontal when fruit has ripened. Fruit presentation at harvest time is excellent and well suited to hand-picking.

Inflorescence: white flowers are borne on short slender pedicels that have no spines (thorns/prickles). At Nelson Region, New Zealand bud burst commences very early, approximately August 20–25, with fifty percent of buds burst by early-mid September (approximately September5–15). The time of bloom is early season for a summer-fruiting raspberry, with peak flowering late October/early November. Corresponding times observed in Lynden, Washington State, USA, typically include bud break commencing at the end of February with 50% buds burst by March 10. Flowering typically begins May 10–20 and peaks in late May. Flowers are numerous and borne on a paniculate inflorescence. Typically, there are five petals, elongated ovate in shape with a rounded apex and flat base. The petals average approximately 6.2 mm in length and 2.9 mm in width. They are typically smooth in texture, have a smooth margin and are near White 155C in color. The pedicel length averages approximately 19.0 mm long. However, the more basal the pedicel the longer it commonly becomes with pedicel lengths up to about 50 mm being observed. The pedicel averages approximately 0.9 mm in diameter and is near Yellow-green 144B in color and like the primocane has quite pronounced anthocyanin coloration on the sun-exposed side (near Red-purple 59A). A typical king flower diameter is approximately 23 mm (from sepal tip to sepal tip i.e. the widest part of the flower). The flowers are predominantly borne singly, although sometimes in clusters of two or more. Terminal branch flower clusters frequently consist of two flowers and basal flower clusters may number three to five. The flowers have no discernible fragrance. Five sepals are present. These are green in coloration (near Green 138C on the top and near Yellow-green 146D on underneath) and measure approximately 8–9 mm in length from base to tip. The reproductive organs are typical for flowers of *Rubus idaeus* L.; the stigmas average approximately 105 in number and are near Yellow-green 145C in color; there are approximately 100 stamens the filaments of which are near White 155C in color and average 3.9 mm in length. Anthers are brown and (depending on maturity) near Brown 200C in color.

Harvest: fruit commences ripening in mid-late November at Motueka, New Zealand; the typical start date for picking the new variety is very early, typically November 22. Fifty percent of the harvest is typically completed by December 12, and the main harvest period is complete by early January (approximately January 4) under New Zealand conditions. In Lynden, Washington State, USA, fruit commonly commences ripening on about June 15–20 and is finished around July 15–20. The early time of fruit ripening has been observed to occur in conjunction with early bud break and a relatively short time from flowering until the onset of fruit ripening. The fruit ripening period for 'Korere' has been observed to be earlier than for other commercial varieties regarded as early season varieties, for instance, 'Glen Moy' (not patented), under New Zealand conditions. 'Korere' is suited to harvest by hand and machine operations. The early fruiting season of 'Korere' is a key distinctive character of the cultivar. 'Korere' is recommended for very early season production for fresh market fruit and has the advantage that later harvests can be machine harvested.

Figure 3:
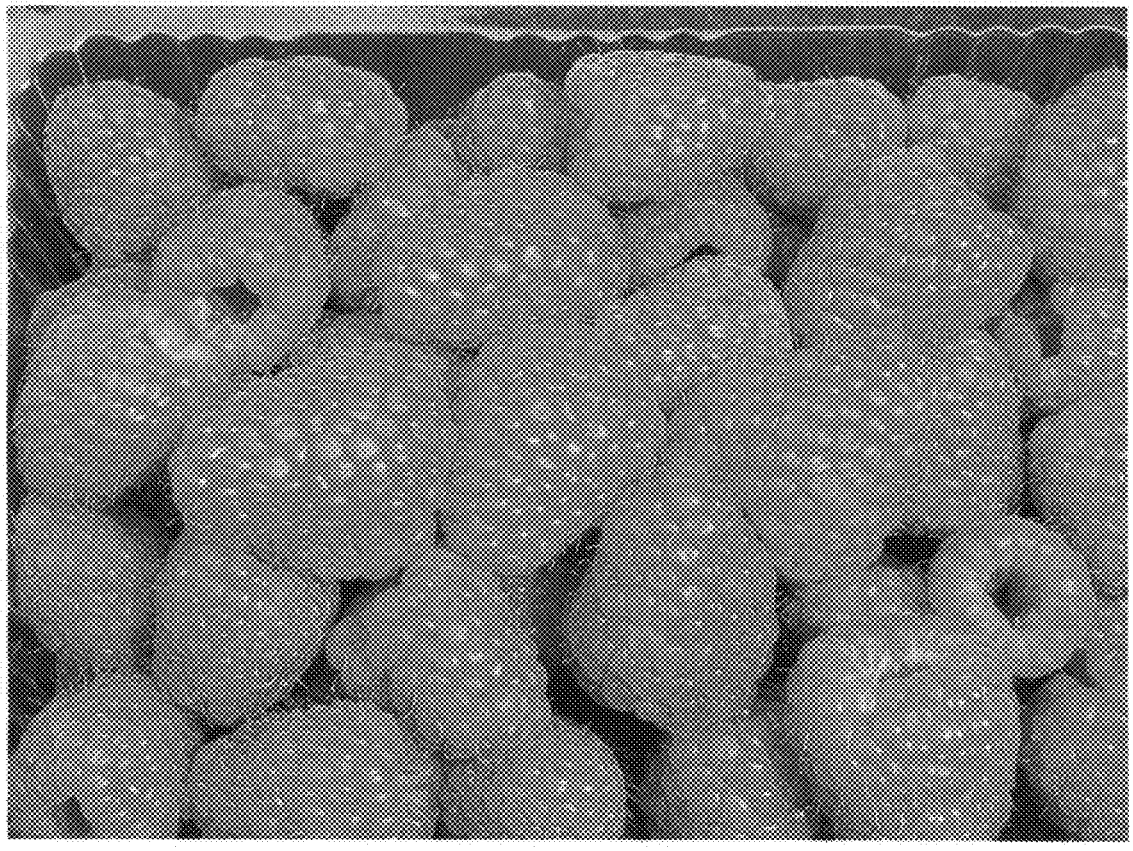
FIG. 3 shows a close-up view of typical fruit of the variety 'Korere'.

Fruit: fruit is produced on previous year's cane in summer. The berries formed on 'Korere' are medium sized. Average berry weight is approximately 3.7 g; individual fruit ranging between 2.5–4.0 g in weight (Table 1). Fruit shape is conical; on the basis of fruit length to width ratio, fruit is longer than broad (FIG. 3). On average berries are 25 mm long and 20 mm wide (at the widest point). Fruit color is medium-red; external color near Red-53A, internal color near Red 46A; and has medium glossiness. Drupelets number typically 107 and are quite distinctively small, typically 3.6 mm in diameter. Although fruit drupelet size has been observed to be small, overall 'Korere' fruit size has been observed to be larger than that for the commercial variety 'Skeena' which has medium size fruit. Fruit quality is largely due to the fruit being medium-firm with good raspberry flavor; fruit firmness has been observed to be more firm than that for fruit from the commercial variety 'Fairview' when grown under New Zealand conditions. The seeds average 2.8 mm long and 1.3 mm wide, and are near Greyed-orange N170C in color when dry. Seed numbers per fruit average 107 and weigh on average 0.21 g per fruit (or on average individually 1.9 mg). 'Korere' fruit has been observed to have a good shelf life in Nelson Region, New Zealand (Table 1). Yield is moderate; the variety is suitable for machine harvesting and hand picking; machine-harvested yields are commonly 4–5 tons per acre in Washington, USA.

Pest and disease resistance: the plant appears to be resistant to Raspberry Bushy Dwarf Virus (RBDV). Since the selection of this clone in 1994–95 numerous tests for RBDV have been carried out on 'Korere' in New Zealand using ELISA, but on no occasion has the virus been detected in spite of high infection pressure. From this we suggest that 'Korere' is likely to be resistant to the common strain of RBDV found in New Zealand. Resistance to aphids is unknown.

Geographical adaptation: observations indicate that the variety is suitable for warmer regions and indications are the variety is also adapted to regions where winter chill is not readily accumulated. 'Korere' performs well in the cool temperate climate of the Nelson region, New Zealand, under standard management practices for commercial raspberry production. Initial indications are that 'Korere' also performs well in USDA plants hardiness zones 8–10 (published as the 2003 US National Arboretum "Web Version" of the USDA Plant Hardiness Zone Map USDA Miscellaneous Publication No. 1475, Issued January 1990) although some winter injury may occur in cooler regions.

It is claimed:

1. A new and distinct red raspberry plant as herein illustrated and described.

* * * * *